(12) United States Patent
Ferguson et al.

(10) Patent No.: US 7,459,285 B2
(45) Date of Patent: Dec. 2, 2008

(54) COMPOUNDS AND METHODS OF USE THEREOF FOR ASSAYING LYSOPHOSPHOLIPASE D ACTIVITY

(75) Inventors: Colin Ferguson, Salt Lake City, UT (US); Glenn Prestwich, Salt Lake City, UT (US)

(73) Assignee: Echelon Biosciences Incorporated, Salt Lake City, UT (US)

( * ) Notice: Subject to any disclaimer, the term of this patent is extended or adjusted under 35 U.S.C. 154(b) by 459 days.

(21) Appl. No.: 10/732,166

(22) Filed: Dec. 9, 2003

(65) Prior Publication Data

US 2004/0171096 A1 Sep. 2, 2004

Related U.S. Application Data

(60) Provisional application No. 60/432,167, filed on Dec. 10, 2002.

(51) Int. Cl.
*C12Q 1/44* (2006.01)
*C12Q 1/34* (2006.01)

(52) U.S. Cl. .......................... 435/19; 435/18

(58) Field of Classification Search ............ 435/18, 435/19
See application file for complete search history.

(56) References Cited

U.S. PATENT DOCUMENTS

| 6,399,392 B1 | 6/2002 | Haugland et al. |
| 2004/0053893 A1 | 3/2004 | Kishimoto et al. |

OTHER PUBLICATIONS

Hendrickson, H. Stewart, et al, "Intramolecularly Quenched BODIPY-Labeled Phospholipid Analogs in Phospholipase A2 and Platelet-Activating Factor Acetylhydrolase Assays and in Vivo Fluroescence Imaging", Analytical Biochemistry 276, 27-35 (1999).
Aoki, J. et al, Serum Lysophosphatidic Acid is Produced Though Diverse Phospholipase Pathways, *J Biol Chem*, vol. 48737-44 (2002).
Bandoh, K. et al, Lysophosphatidic acid (LPA) receptors of the EDG family are differentially activated by LPA species, *FEBS Lett*, vol. 478, 159-65 (2000).
Clair, T. et al, Autotaxin Hydrolyzes Sphingosylphosphorylcholine to Produce the Regulator of Migration, Sphingosine-1-Phosphate, *Cancer Research*, vol. 63, 5446-53 (2003).
Farber, S. et al, Characterization of $Ca^{2+}$ dependent Phospholipase $A_2$ Activity during Zebrafish Embryogenesis, *J Biol Chem*, vol. 274, 19338-46 (1999).
Fang, X. et al, Lysophospholipid Growth Factors in the Initiation, Progression, Metastases, and Management of Ovarian Cancer, *Ann NY Acad Sci*, vol. 905, 188-208 (2000).
Feng, L. et al, A Real-Time Flurogenic Phospholipase $A_2$ Assay for Biochemical and Cellular Activity Measurements—*Chemistry & Biology*, vol. 9, 795-803 (2002).
Heise, C. et al, Activity of 2-Substituted Lysophosphatidic Acid (LPA) Analogs at LPA Receptors: Discovery of a $LPA_1/LPA_3$ Receptor Antagonist, *Mol Pharmacol*, vol. 60, 1173-80 (2001).
Hendrickson, H. et al, Evaluation of Fluorescent and Colored Phosphatidylcholine Analogs as Sustrates for the Assay of Phospholipase $A_2^1$, *Analyt Biochem*, vol. 185, 80-3 (1990).
Hla, T. et al, Lysophospholipids—Receptor Revelations, *Science*, vol. 294, 1875-8 (2001).
Imamura, F. et al, Induction of In Vitro Tumor Cell Invasion of Cellular Monolayers by Lysophosphatidic Acid or Phospholipase D, *Biochem Biophy Res Commun*, vol. 193, 497-503 (1993).
Luquain, C. et al, Lysophosphatidic acid signaling: how a small lipid does big things, *Trends Biochem Sci*, vol. 28, 377-83 (2003).
Mills, G. et al, A Putative New Growth Factor in Ascitic Fluid from Ovarian Cancer Patients: Identification, Characterization, and Mechanism of Action, *Cancer Res*, vol. 48, 1066-71 (1988).
Mills, G. et al, Critical Role of Lysophospholipids in the Pathophysiology, Diagnosis, and Management of Ovarian Cancer, *Cancer Treat Res*, vol. 107, 259-83 (2002).
Mills, G. et al, Future for Ovarian Cancer Screening: Novel Markers from Emerging Technologies of Transcriptional Profiing and Proteomics, *J Natl Cancer Inst*, vol. 93, 1437-9 (2001).
Moolenaar, W. et al, Lysophosphatidic acid: G-protein signalling and cellular responses, *Curr Opin Cell Bio*, vol. 9, 168-73 (1997).
Moolenaar, W., Bioactive Lysophospholipids and Their G Protein-Coupled Receptors, *Exp Cell Res*, vol. 253, 230-8 (1999).
Nam, S., et al, Autotaxin (ATX), a potent tumor motogen, augments invasive and metastatic potential of ras-transformed cells, *Oncogene*, vol. 19, 241-7 (2000).
Nieuwenhuizen, W. et al, Synthesis of a novel fluorescent ceramide analogue and its use in the characterization of recombinant ceramidase from *Pseudomonas aeruginosa* PA01, *Chem Phys Lipids*, vol. 114, 181-91 (2002).
Pankuch, J. et al, N-Me-pAB-Glu-y- Glu-y-Tyr(3-$NO_2$): An Internally Quenched Fluorogenic y-Glutamyl Hydrolase Sustrate, *Bioorg Med Chem Lett*, vol. 11, 1561-4 (2001).
Sandro, S. et al, Quencher as Leaving Group: Efficient Detection of DNA-joining Reasctions, *J Am Chem Soc*, vol. 124, 2096-7 (2002).
Stassar, M. et al, Identification of human renal cell carcinoma associated genes by suppression subtractive hybridization, *Br J Cancer*, vol. 85, 1372-82 (2001).

(Continued)

*Primary Examiner*—Irene Marx
*Assistant Examiner*—Susan Hanley
(74) *Attorney, Agent, or Firm*—The McCallum Law Firm, P.C.; Jennifer M. McCallum, Esq.

(57) ABSTRACT

Fluorogenic lysophosphatidic acid derivatives which can be used as substrates in a continuous, fluorogenic assay that can be performed in microtiter plates. The assays permit measuring LysoPLD activity levels in normal events such as pregnancy or disease states such as cancer. In addition, the present invention can be adopted to high throughout screening(HTS) for identification of potential inhibitors of lysoPLD activity.

6 Claims, 9 Drawing Sheets

OTHER PUBLICATIONS

Tokumura, A. et al, Involvement of Iysophospholipase D in the production of Iysophosphatidic acid in rat plasma, *Biochim Biophys Acta*, vol. 875, 31-8 (1986).

Tokumura, A., Physiological and pathophysiological roles of lysophosphatidic acids produced by secretory lysophospholipase D in body fluids, *Biochimica et Biophysica Acta*, vol. 1582, 18-25 (2002).

Tokumura, A. et al, Identification of Human Plasma Lysophospholipase D, a Lysophosphatidic Acid-producing Enzyme, as Autotaxin, a Multifunctional Phosphodiesterase, *J Biol Chem*, vol. 277, 39436-42 (2002).

Tokumura, A. et al, Increased formation of lysophosphatidic acids by lysophospholipase D in serum of hypercholesterolemic rabbits, *J Lipid Res*, vol. 43, 307-15 (2002).

Tyagi, S. et al, Molecular Beacons: Probes that Fluoresce upon Hybridization, *Nat Biotechnol*, vol. 14, 303-8 (1996).

Umezu, M. et al, Autotaxin has lysophospholipase D activity leading to tumor cell growth and motility by lysophosphatidic acid production, *Journal of Cell Biology*, vol. 158, 227-33 (2002).

Xu, Y. et al, The Role and Clinical Applications of Bioactive Lysolipids in Ovarian Cancer, *J Soc Gynecol Investig*, vol. 8, 1-13 (2001).

Xu, Y. et al, Characterization of an Ovarian Cancer Activating Factor in Ascites from Ovarian Cancer Patients, *Clin Cancer Res*, vol. 1, 1223-32 (1995).

Yang, S. et al, Expression of autotaxin (NPP-2) is closely linked to invasiveness of breast cancer cells, *Clin Exp Metastasis*, vol. 19, 603-9 (2002).

Yang, Y. et al, Autotaxin Expression in Non-Small-Cell Lung Cancer, *Am J Respir Cell Mol Biol*, vol. 21, 216-22, (1999).

Zhang, G. et al, Expression of autotaxin mRNA in human hepatocellular carcinoma, *Chin Med J (Engl)*, vol. 112, 330-2 (1999).

Zaikova, T. et al, Synthesis of Fluorogenic Substrates for Continuous Assay of Phosphatidylinositol-Specific Phospholipase C, *Bioconjugate Chem*, vol. 12, 307-13 (2001).

A = O or S
B = H, Na⁺, K⁺, Li⁺, any alkyl group, E = O, CH$_2$, CHF CF$_2$
G = H, OH, F, Oacyl, Oalkyl, K$_1$ or K$_2$ = H, F, any alkyl, CO$_2$H
W = C(O), NH(CH$_2$)$_m$, [NHC(O)(CH$_2$)$_n$]$_p$C(O), NH(CH$_2$CH$_2$O)$_q$C(O)
    m = 1-10, n = 1-12, p = 1-20, q = 1-33
X = NH, N(CH$_3$)$_2$, CH$_2$, Y = O, S, NH
Z = C(O), (CH$_2$)$_m$NH, [C(O)(CH$_2$)$_n$]$_p$C(O)NH, (CH$_2$CH$_2$O)$_q$C(O)NH
R$_1$ = flourescent or quencher group, R$_2$ = quencher or flourescent group

COMPOUNDS AND METHODS OF USE THEREOF FOR ASSAYING LYSOPHOSPHOLIPASE D ACTIVITY

This application claims priority of the U.S. Application Ser. No. 60/432,167, filed on Dec. 10, 2002.

BACKGROUND OF THE INVENTION

1. Field of the Invention

The present invention relates generally to lipid metabolism. More particularly, the present invention relates to non-radioactive assays for the detection of the lysophospholipase D(LysoPLD) activity by measuring the metabolism of a synthetic substrate analog.

2. Related Art

The role of lipids in cancer development is being recognized as being extremely important and they provide new targets for therapeutics. Many bioactive lysophospholipids, including LPA, LPC, sphingosylphosphorylcholine (SPC), sphingosine 1-phosphate (S1P) and lysophosphatidylserine (lyso-PS) exhibit pleiomorphic effects on multiple cell lineages, including ovarian cancer cells.(Fang, et al., Ann. N.Y. Acad. Sci., 905:188-208. (2000, Luquain, et al., Trends Biochem. Sci., 28:377-83. (2003)) LPA and S1P signal through interaction with specific cell surface receptors of the endothelial cell differentiation gene (edg) family of cell surface seven-transmembrane G-protein coupled receptors (GPCR), whereas SPC and LPC activate the OGR 1 family of GPCR. (Hla, et al., Science, 294:1875-8. (2001)) LPA is formed by two routes as shown in FIG. 1, hydrolysis of the sn-2 acyl chain of phosphatidic acid (PA) by a PA-specific $PLA_2$ or by cleavage of the choline head group from lyso-phosphatidylcholine by LysoPLD. The purification, characterization, and identification of the ovarian cancer activating factor (OCAF) from ascites fluid of ovarian cancer patients has demonstrated that OCAF is comprised of numerous forms of LPA, and accounts for the ability of ascites fluid to activate ovarian cancer cells.(Mills, et al., Cancer Res., 48:1066-71. (1988)) LPA, at concentrations present in ascites fluid from ovarian cancer patients (1-80 µM), increases proliferation under anchorage-dependent and -independent conditions, prevents apoptosis and anoikis, increases invasiveness, induces cytoskeletal reorganization and change of shape; decreases sensitivity to cisplatin (the most effective drug in the treatment of ovarian cancer), increases production of vascular endothelial growth factor (VEGF), interleukin-8 (IL8), IL6, urokinase-type plasminogen activator (uPA), and LPA itself, increases activity of matrix metalloprotease-2 (MMP2) and MMP9, and increases mRNA expression for a number of growth factors and other important mediators.(Mills, et al. Cancer Treat. Res., 107:259-83. (2002). Thus LPA plays a critical role in the regulation of proliferation, viability, drug sensitivity, invasiveness and metastasis of ovarian cancer cells, suggesting that it is likely to be an effective target for therapy.

The LPA receptors edg-2, edg-4, and edg-7 are now known as $LPA_1$, $LPA_2$, and $LPA_3$, respectively. Pharmacological concentrations of LPA must be produced extracellularly to induce receptor-dependent biological responses.(Moolenaar, et al., Curr. Opin. Cell Biol., 9:168-73. (1997)) LPA receptors exhibit characteristic responses to LPA species with different chain lengths, different unsaturation patterns, and different acyl positions.(Bandoh, et al., FEBS Lett., 478:159-65. (2000)) In addition, LPA receptors can show marked enantioselectivity as well as isoform-selective activation for a series of 2-substituted N-oleoyl ethanolamide phosphoric acid (NAEPA) analogs.(Heise, et al., Mol. Pharmacol., 60: 1173-80. (2001)) For example, LPA produced by stimulated platelets(Moolenaar, et al., Curr. Opin. Cell Biol., 9:168-73. (1997), Moolenaar, Exp. Cell Res., 253:230-8. (1999)) is distinct from the LPA found in ascites fluid from ovarian cancer patients(Mills, et al., J. Natl. Cancer. Inst., 93:1437-9. (2001)), and is an important bioactive lipid in ovarian cancer. (Mills, et al., Cancer Treat. Res., 107:259-83. (2002, Xu, et al., J. Soc. Gynecol. Investig., 8:1-13. (2001)) In platelets, sn-1 LPA is preferentially produced, but ascites fluid contains an elevated amount of sn-2 LPA.(Xu, et al., Clin. Cancer Res., 1:1223-32. (1995)) Lysophospholipase D activity was first characterized over sixteen years ago and recognized as an important source of plasma LPA.(Tokumura, et al., Biochim. Biophys. Acta, 875:31-8. (1986)) At least two forms are known—one which degrades alkyl ether linked LPC (i.e., platelet activating factor, or PAF) which is calcium-dependent and intracellular. The other form, secreted into the plasma, optimally processes acyl-linked LPC but will also hydrolyze PAF and sphingosylphosphocholine.

LysoPLD has an important role in normal physiology. This enzymes activity is increased in normal pregnant women in the third trimester, correlating with the role of LPA in stimulating oocyte maturation and embryonic development. FIG. 1 illustrates the normal route of LPA formation and cell activation, in which conversion of PC to LPC in high-density lipoprotein particles from the liver is coupled to lecithin cholesterol acyltransferase which converts cholesterol (Chol) to cholesteryl esters (CE).(Tokumura, Biochimica et Biophysica Acta—Molecular and Cell Biology of Lipids, 1582: 18-25. (2002)) LPC is the second most abundant phospholipid in human serum, with an estimated concentration of 200 µM.(Tokumura, et al., J. Biol. Chem., 277:39436-42. (2002)) LPC can also be produced by the hydrolysis of PC by $PLA_1$ or $sPLA_2$ released from activated cells or tumor cells. The pathophysiology of lysoPLD is also noteworthy. It is upregulated in ascites fluid and serum of patients with ovarian cancer and the LPA thus produced can enhance metastasis of cancer cells through mesothelial cell layers. Imamura, et al., Biochem Biophys Res Commun, 193:497-503. (1993) In addition, it is overproduced in hypercholestermic rabbits causing monocyte activation and attachment to vascular walls, leading to atherosclerosis from increased LPA levels.(Tokumura, et al., J Lipid Res, 43:307-15. (2002)).

Recently, lysoPLD has been purified and cloned. The purified lysoPLD from human serum has increased activity by 14,400-fold, a $K_m$ of 260 µM and a $V_{max}$ of 103 nmol/min for 16:0 LPC. Similar kinetic parameters were obtained for unpurified human ATX expressed in CHO-K1 cells. LysoPLD/ATX processed LPC more effectively than nucleotides.(Tokumura, et al., J. Biol. Chem., 277:39436-42. (2002)) Comparison with proteins in the database revealed the identity as being ATX, an enzyme previously thought to cleave nucleoside di- and trisphosphates. Cloned rat and human ATX exhibit identical activities to serum lysoPLD.

Autotaxin (ATX) was known as NPP2 and is a 125-kDa glycoprotein that stimulates tumor cell motility and has an in vivo role in tumor progression and invasion.(Nam, et al., Oncogene, 19:241-7. (2000)) ATX/LysoPLD belongs to the nucleotide pyrophosphatase/phosphodiesterase (NPP) family of enzymes which release the nucleoside 5'-phosphate from nucleotide and nucleotide derivatives. Increased ATX mRNA and/or expression levels have been demonstrated in several cancers including ovarian, breast(Yang et al., Clin.

Exp. Metastasis, 19:603-608 (2002) hepatocellular(Zhang et al., Chin Med J (Engl) 112:330-2. (1999)), lung(Yang et al. Am J Respir Cell Mol Biol. 21:216-22. (1999)), prostate, colon, renal carcinoma (Stassar et al, Br J Cancer, 85:1372-82. (2001)), and Hodgkin's lymphoma.

Recent work has shown that loss of LysoPLD activity in ATX mutants results in a reduction in motogenic ability, directly demonstrating that the production of bioactive phospholipids (i.e. LPA) is important for cell motility. This result suggests that inhibition of increased ATX/LysoPLD activity by small-molecules could be an attractive new avenue for anti-cancer chemotherapy.

Early methods for assaying LysoPLD activity were performed with $^{14}$C-palmitoyl-LPC and radio-thin layer chromatography (TLC). This was supplanted by TLC purification of unlabeled LPA with GC analysis of methyl esters, or by measurement of LPA-trimethylsilyl ether by gas chromatography-mass spectrometry (GC-MS). Recently, an enzymatic determination of choline release has been employed. However, none of the existing methods are suited to HTS (high throughput screening) and drug discovery. Assays using fluorogenic substrates have become widely utilized because of high sensitivity, ease of handling, adaptability for HTS) formats, and the ability to follow the kinetics of the reaction without the need for quenching at each time point. Importantly, fluorogenic assays permit continuous monitoring rather than needing be stopped at various endpoints, and they can be adapted from an in vitro biochemical modality to a cell-based in sits assay. One common modality is the conversion of a non-fluorescent substrate, e.g., a fluorescein phospholipid ester, to a fluorescent product.(Zaikova, et al., Bioconjugate Chem., 12:307-13. (2001))

A more complex and versatile approach, employs a "fluorescence dequenching" mode, in which a fluorophore that is "silent" because of intramolecular quenching becomes fluorescent once enzymatic activity liberates it from the intramolecular energy transfer mechanism. Such an approach was demonstrated for PLA$_2$(Feng, et al., Chemistry & Biology, 9:795-803. (2002)) and the assay for lysoPLD of the present invention(FIG. 2). Other fluorogenic assays have been developed to monitor ceramidase(Nieuwenhuizen, et al., Chem. Phys. Lipids, 114:181-91. (2002)), γ-glutamyl hydrolase, DNA ligase(Sando, et al., J. Am. Chem. Soc., 124:2096-7. (2002, Pankuch, et al., Bioorg. Med. Chem. Lett., 11:1561-4. (2001)), PLA$_2$ (Hendrickson, et al., Analyt. Biochem., 185: 80-3. (1990, Farber, et al., J. Biol. Chem., 274:19338-46. (1999)), and nucleic acid hybridization.(Tyagi, et al., Nat. Biotechnol., 14:303-8. (1996))

SUMMARY OF THE INVENTION

It has been recognized that it would be advantageous to develop homogenous HTS-compatible methods for detecting the LysoPLD activity of ATX and for use thereof in disease detection and drug discovery.

The present invention provides a non-radioactive assay for the detection of the LysoPLD activity of ATX by measuring the metabolism of a synthetic substrate analog incorporating both a fluorophore and a quencher. When the enzyme metabolizes the substrate, there is a quantifiable increase in fluorescence. The assay is amenable to HTS and can be used for drug discovery and disease detection.

One aspect of the present invention relates to the synthesis of fluorogenic substrates.

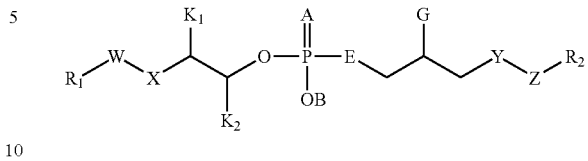

wherein A represents O or S, B represents H, Na$^+$, K$^+$, Li$^+$, or an alkyl group with 1-20 carbons, E represents O, CH$_2$, CHF or CF$_2$, G represents H, OH, F, Oacyl or Oalkyl with 1-20 carbons, K$_1$ and K$_2$ represent H, F, an alkyl with 1-20 carbons, OH, or CO$_2$H, W represents C(O), NH(CH$_2$)$_m$, [NHC(O) (CH$_2$)$_n$]$_p$C(O) or NH(CH$_2$CH$_2$O)$_q$C(O) wherein m is an integer from 1 to 10, n is an integer from 1 to 12, p is an integer from 1 to 20, q is an integer from 1 to 33, X represents NH, N(CH$_3$)$_2$ or CH$_2$; Y represents O, S or NH; Z represents C(O), (CH$_2$)$_m$NH, [C(O)(CH$_2$)$_n$]$_p$C(O)NH or (CH$_2$CH$_2$O)$_q$C(O) NH; R$_1$ and R$_2$ is a fluorescent group or a quencher group, respectively.

In addition, Q could be a fluor, which undergoes fluorescence resonance energy transfer (FRET) with F making the molecule applicable to a FRET assay. In addition, Q could be a lanthanide chelate or cryptate for use in a time resolved-FRET (TR-FRET) assay. Another aspect of the present invention relates to using said substrates in an assay for the LysoPLD activity of purified ATX. Another aspect of the present invention relates to optimizing the assay for detection of LysoPLD activity in patient samples, such as serum, plasma, and ascites fluid. One embodiment of the present invention provides an assay that can be used as a screening tool for inhibitors of LysoPLD activity, which could be novel anti-cancer agents.

The present invention provides substrates and assays to probe lysoPLD in a continuous, fluorogenic assay that can be performed in microtiter plates. The design of the assays of the present invention permits measuring LysoPLD activity levels in normal events such as pregnancy or disease states such as cancer. In addition, the present invention can be adopted to high throughout screening(HTS) for identification of potential inhibitors of lysoPLD activity. In addition, the present invention can be used to monitor the status of a patient receiving a medication designed to alter the activity of LysoPLD in a pharmaceutical context.

Additional features and advantages of the invention will be apparent from the detailed description which follows, which when taken in conjunction with the accompanying drawings, together illustrate, by way of example, features of the invention.

DETAILED DESCRIPTION

Figure 1:
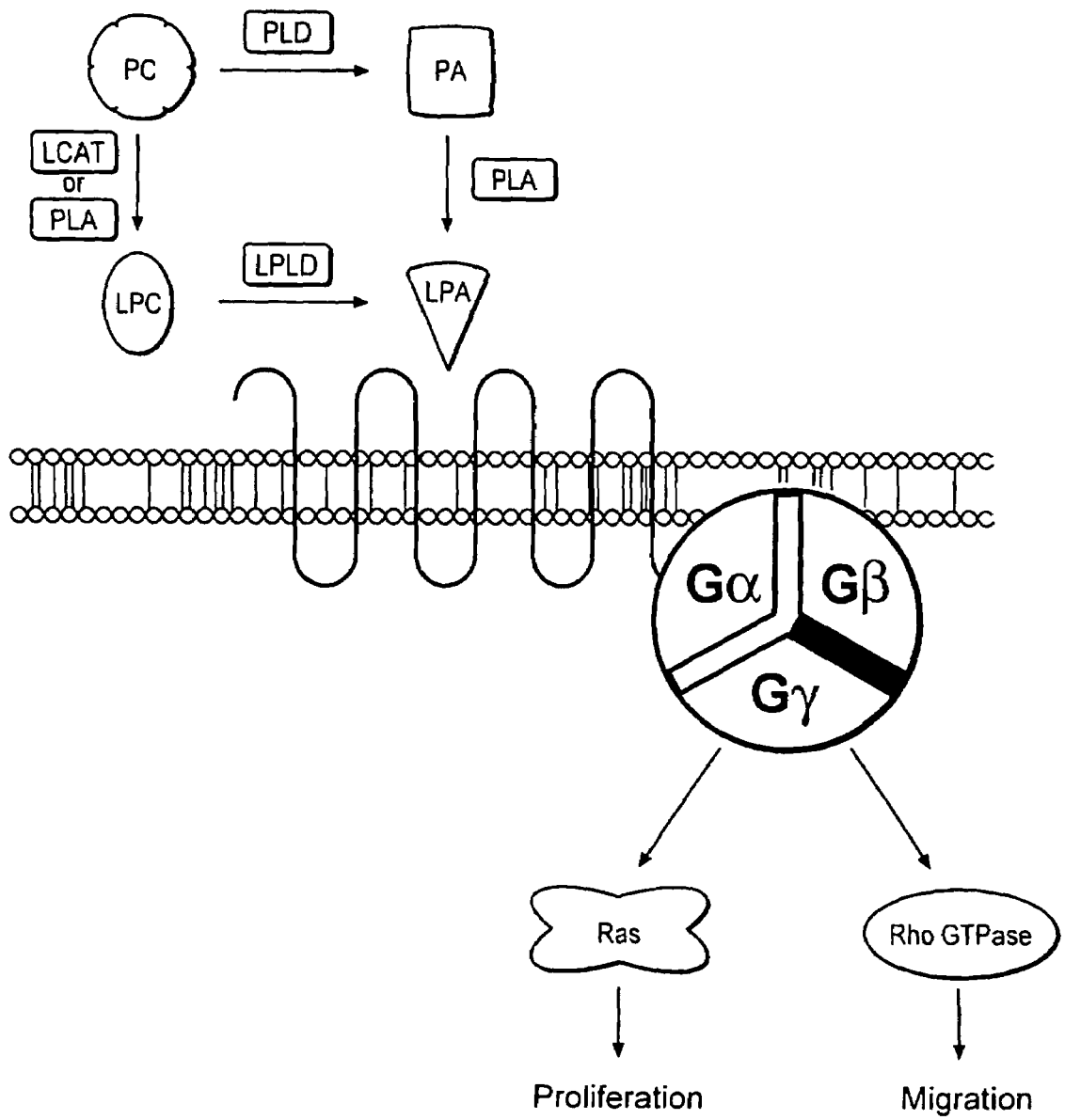
FIG. 1 shows a diagram of the pathways of LPA formation and activation of receptors.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

Figure 2:
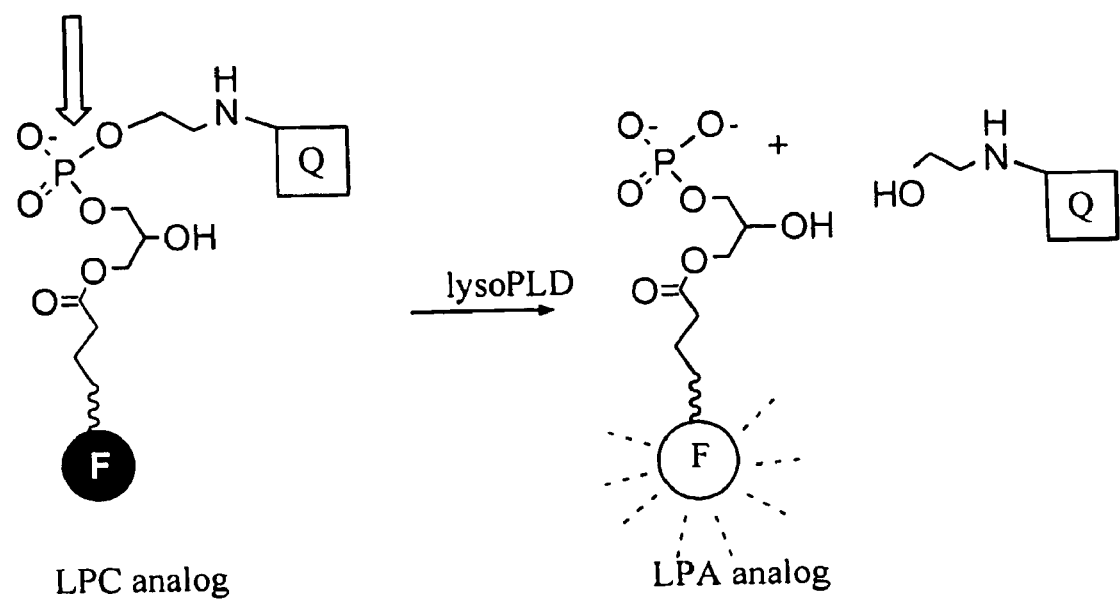
FIG. 2 illustrates the concept of the fluorogenic LysoPLD assay.

FIG. 2 illustrates the assay scheme for the embodiment of the present invention. The substrates are doubly labeled derivatives of lysophospholipids in which one label is a fluorescent group(hereafter referred as "fluor") and the other is designated as the quencher group(hereafter referred as "quencher"). Intramolecular energy transfer between the fluor and the quencher attenuates the fluorescent output of the molecule. When the fluor and quencher become physically separated, by enzymatic cleavage of the ethanolamino headgroup from the substrate, the quencher can no longer absorb energy from the fluor and a fluorescent signal can be measured. The fluorescent signal measured is proportional to the degree of metabolism of the substrate by the enzyme.

Figure 3:
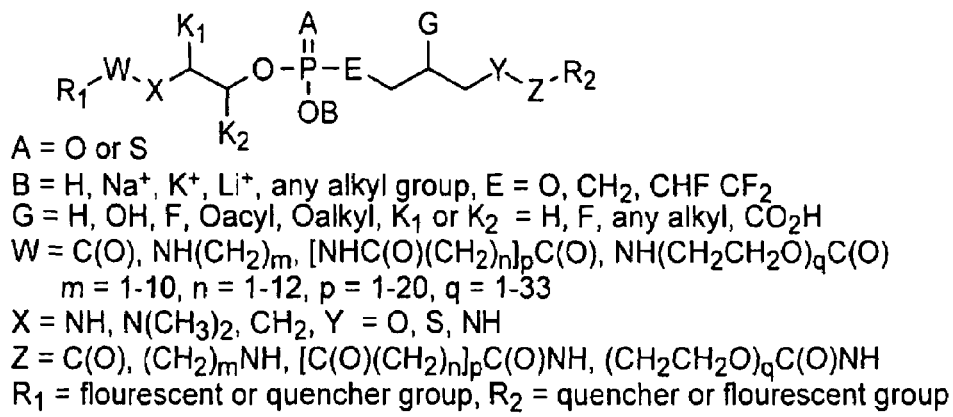
FIG. 3 shows a general LysoPLD substrate structure.

LysolPLD is reported to hydrolyze a variety of acyl chain modifications(Tokumura, et al., J. Biol, Chem., 277:39436-42. (2002)) and head group types. It is also tolerant to changes in the backbone and headgroup, hydrolyzing lysophosphatidylserine, lysophosphatidylethanolamine (LPE), lysophosphatidylinositol, (Aoki, et at., J. Biol. Chem., 277:48737-44. (2002)) and sphingosylphosphorylcholine. (Clair, et at., Cancer Research, 63:5446-53. (2003)) Thus, as summarized in FIG. 3, a general substrate structure is described where F = fluorescent group and Q = quencher group. A fluorescent group is defined as any chemical moiety which absorbs light at a given wavelength and emits light at a higher wavelength e.g. fluorescein, tetramethylrhodamine, and BODIPY-FL® (4,4-difluoro-5,7-dimethyl-4-bora-3a,4a-diaza-/s/-indacene) (hereinafter "BODIPY-FL®). A quencher is described as any moiety which absorbs light at a given wavelength but does not fluoresce e.g. DABCYL, 2,4 dinitrophenyl, and QSY-7® (Xanthylium, 9- [2-[4-[[(2,5-dioxo-1-pyrrolidinyl)Oxy]-1-piperidinyl]sulfonvl]phenyl]-3,6--, chloride) (hereinafter OSY-7®). In any case, the relative positions of the fluorescent and quencher groups can be reversed. In addition, Q could be a fluor, which undergoes fluorescence resonance energy transfer (FRET) with F making the molecule applicable to a FRET assay. In addition, Q could be a lanthanide chelate or cryptate for use in a time resolved-FRET (TR-FRET) assay.

Figure 4:
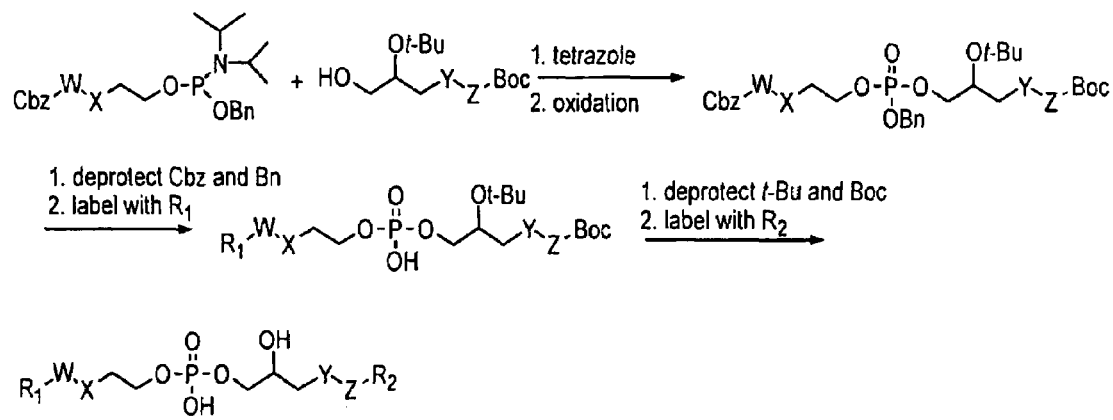
FIG. 4 demonstrates a general synthetic route to the substrates.

Four fluorescence-quenched, fluorogenic substrates (FS-1, FS-2, FS-3 and FS-7) were prepared as described below. Initially the variation in fluor/quencher pairings was minimized, simplifying comparisons and synthetic design. However, other fluor/quencher combinations are covered by this invention. A general synthetic route is described in FIG. 4.

The first two components are coupled by standard phosphoramidite chemistry to form the phosphite followed by oxidation to the phosphate. The benzyl (Bn) and carbobenzyloxy (Cbz) groups are removed e.g. by catalytic hydrogenation and the molecule is labeled with $R_1$. The tert-butyl group (t-Bu) and tert-butoxycarbonyl (Boc) groups are removed under acidic conditions and the molecule is labeled with $R_2$. $R_1$ and $R_2$ is a fluorescent group or a quencher group, respectively.

Figure 5:
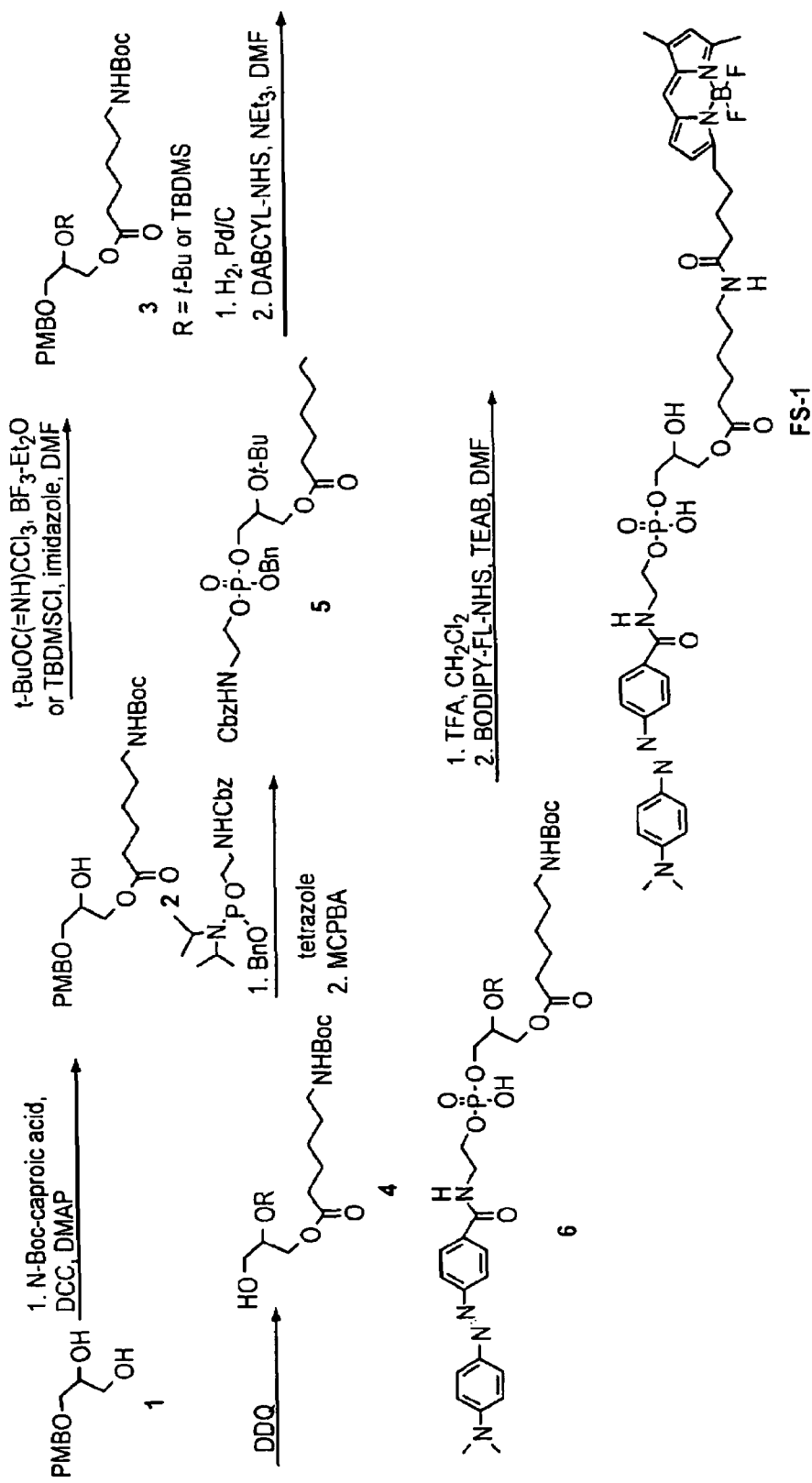
FIG. 5 shows the synthetic scheme for the synthesis of FS-1.

The first substrate (FS-1) was synthesized as described in FIG. 5, having BODIPY-FL®Molecular Probes Inc., Oregon) as the fluor and DABCYL as the quencher. Starting with p-methoxybenzyl (PMB) protected glycerol 1, the primary hydroxyl was selectively acylated with N-carbobenzyloxy (Cbz)-caproic acid forming 2. The sn-2 hydroxyl was protected as the tert-butyl (R=t-Bu) ether forming 3 followed by deprotection of the PMB group with 2,3-dichloro-5,6-dicyanobenzo-1,4-quinone (DDQ) forming 4. The sn-3 hydroxyl was phosphitylated with phosphoramidite 5 (prepared from N-Cbz-ethanolamine and benzyl bisdiisopropylphosphoramidite) then oxidized with 3-chloroperbenzoic acid (MCPBA) to yield 6. Catalytic hydrogenation cleaved the benzyl and Cbz groups and the free amine was coupled to the quencher group, 4-((4-(dimethylamino)phenyl)azo)benzoic acid (DABCYL), via the activated ester of N-hydroxysuccinimide (NHS) 7. The Boc and t-Bu groups were removed by treatment with TFA in dichloromethane and the resulting amine was labeled with the fluor, BODIPY-FL® by the ester of NHS yielding FS-1. A subsequent revision of the synthetic scheme replaced the t-Bu group with a tert-butyldimethylsilyl (TBDMS) group improving the overall synthetic yield.

Figure 6:
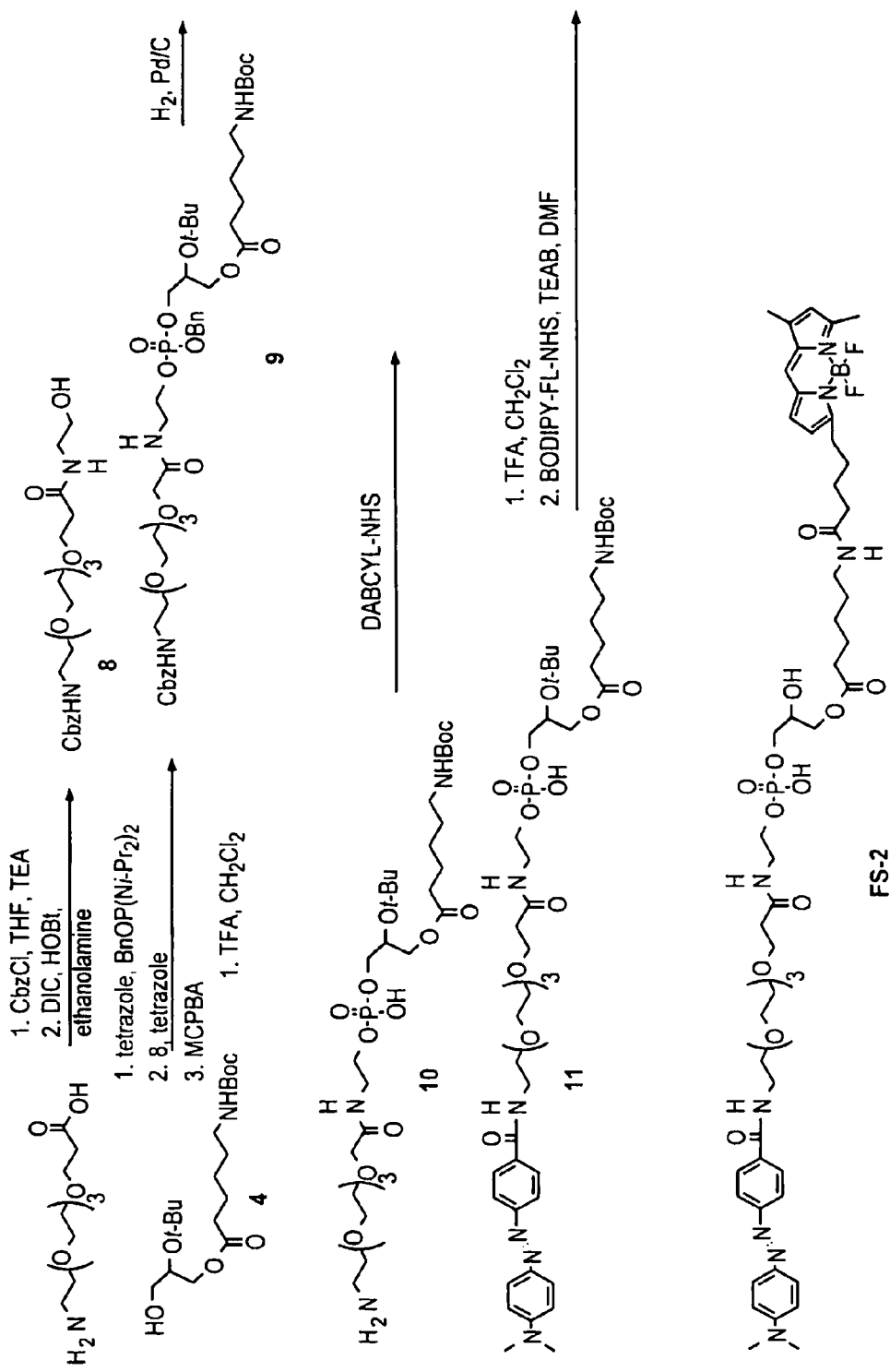
FIG. 6 shows the synthetic scheme for the synthesis of FS-2.

The second substrate (FS-2), which retains the quencher in the head group and fluor in the acyl chain, was synthesized in a route similar to that employed in FIG. 5, with the modification that a short hydrophilic spacer composed of three ethylene glycol units was inserted into the headgroup. The linker (8) was prepared from a commercially available $PEG_4$ amino acid as shown in FIG. 6. The amino group of the $PEG_4$ was protected with a Cbz group and the carboxyl group was coupled to ethanolamine by diisopropylcarbodiimide (DIe). 8 was coupled to the benzyl diisopropylphosphoramidite of 4 with a tetrazole forming the phosphite and then immediately oxidized with MCPBA. Once the protected phosphate 9 was prepared, it was subjected to catalytic hydrogenation to remove the benzyl and Cbz groups yielding 10. The free amine was coupled with DABCYL-NHS forming 11. Treatment with TFA cleaved the tert-butyl and Boc groups and the resulting amino group was conjugated to the NHS activated ester of BODIPY-FL® forming FS-2.

Figure 7:
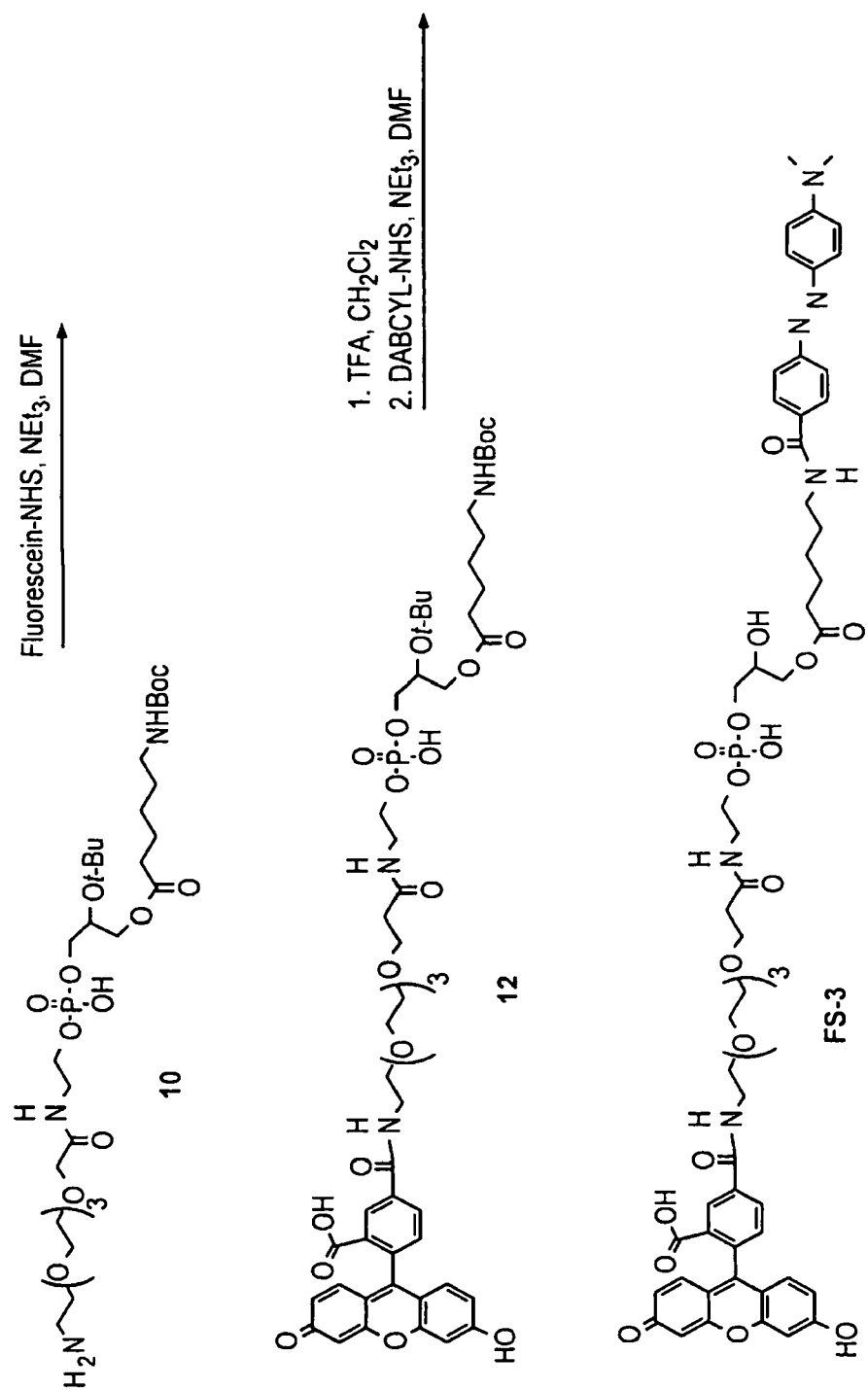
FIG. 7 shows the synthetic scheme for the synthesis of FS-3.

In FS-3 the relative positions of the fluor and quencher were varied, knowing that the Dabcyl-ω-aminohexanoate is sufficiently hydrophobic to mimic an acyl group in both in vitro and cell-based enzyme assays. Because BODIPY-FL® is too hydrophobic to effectively mimic a head group, fluorescein was selected as the head group fluor. This was accomplished, as outlined in FIG. 7, by coupling the amine 10 using NHS-activated fluorescein thereby forming 12. The tert-butyl and Boc groups were removed with TFA and the amino group was labeled with DABCYL-NHS to form FS-3.

Figure 8:
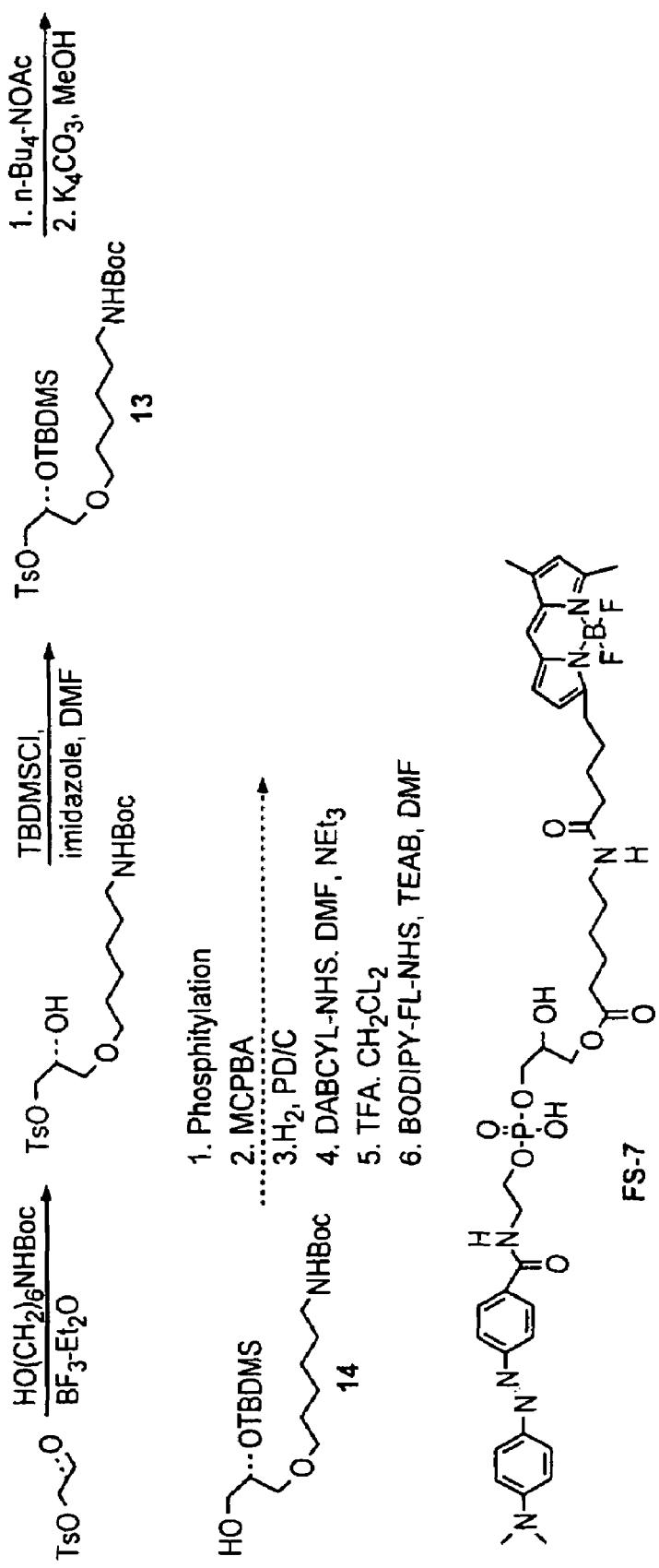
FIG. 8 shows the synthetic scheme for the synthesis of a precursor to FS-7.

For FS-7 (X=O), the sn-1 glyceryl ester was replaced with a more robust ether linkage. The ether-linked glycerol (14) was prepared as described in FIG. 8 adapting a method described by Kazi et al.(Kazi, et al., J. Org. Chem., 64:9337-47. (1999)) Tosyl protected (S)-glycidol was opened by Boc-aminohexanol in the presence of $BF_3$-etherate, followed by protection of the sn-2 hydroxyl as the TBDMS ether (13). Displacement of the tosyl group by tetrabutylammonium acetate and subsequent deacetlyation yielded the ether glycerol 14. Conversion to FS-4 followed the same phosphitylation, oxidation, deprotection, and labeling steps as demonstrated for FS-1, FS-2, and FS-3.

Figure 9:
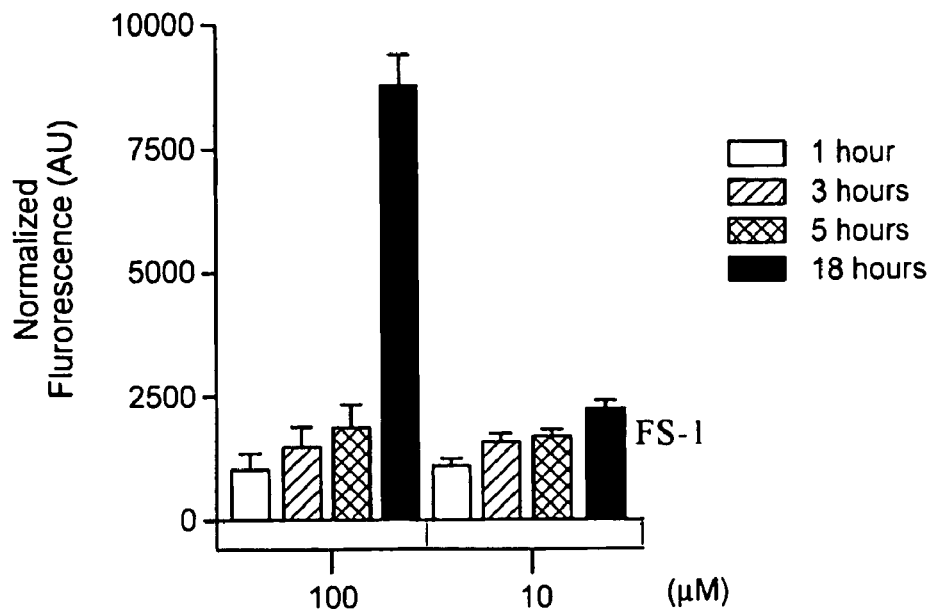
FIG. 9 shows the turnover of substrate FS-1 in human plasma.

FIG. 9 illustrates the evaluation of the fluorogenic substrate FS-1 using fetal bovine serum which is known to be a rich source of LPA that is "self-regenerating" through the in situ activity of lysoPLD.(Umezu-Goto, et al., Journal of Cell Biology, 158:227-33. (2002)) A 10 mM stock solution of FS-1 in MeOH was added to 50 µL solutions of 1% or 10% FBS in PBS and incubated at 25° C. overnight. Measurements were taken on a Hewlett Packard Fusion instrument at 1, 3, 5, and 18 hours. In this unoptimized assay, the substrate FS-1 is apparently cleaved by the lysoPLD to give an increase in fluorescence with time. The observed increase is sensitive to the quantity of FBS used, with higher enzyme concentrations affording higher presumed conversion of the quenched FS-1 to a fluorescent LPA analog. In addition, the fluorescence increase was dependent on substrate concentration, with the optimal conversion being observed at 100 µM. This closely approximates the published $K_m$ value for the purified recombinant human ATX/lysoPLD enzyme, and the expected turnover for the FBS-derived enzyme. This increase in fluorescence was not present in serum that had been boiled for 10 min to inactivate the enzymatic activity.

Figure 10:
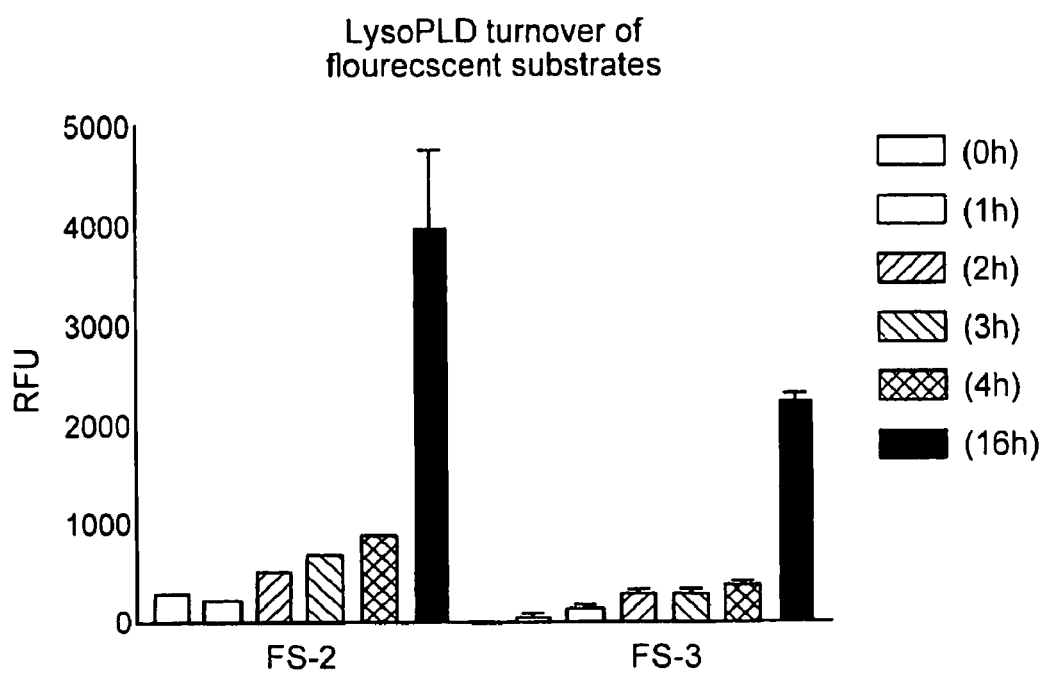
FIG. 10 illustrates the turnover of FS-2 and FS-3 by partially purified human LysoPLD.

The substrates of the present invention can be used to measure the activity of purified or partially purified enzymes in an in vitro assay. LysoPLD can be purified from human plasma (Tokumura, et al., J. Biol. Chem., 277:39436-42. (2002)) or can be obtained as a recombinant protein. The enzyme stock solution is diluted to the desired concentration in PBS or TBS in the wells of a 384-well white or black microtiter plate to give a final volume of 50 µL. A stock solution of the IFS substrate in MeOH or water is added to give a final concentration between 1 and 100 µM. Fluorescence is measured on a plate reader using the particular excitation and emission wavelengths for the fluorescent group on the substrate. As the enzyme metabolizes the substrate an increase in fluorescence is recorded. FIG. 10 illustrates the increase in fluorescence recorded over time with substrates FS-2 and FS-3 being metabolized by LysoPLD partially purified from human plasma.

Since the action of ATX/lysoPLD is recognized as an important factor in ovarian and other types of cancer, it becomes an attractive target for drug discovery efforts. Attenuating the activity of the enzyme offers another route to treating ovarian cancer. Using the fluorescent LysoPLD substrates and in vitro assays for LysoPLD activity provided by the present invention, libraries of small molecules can be screened for inhibitors of the enzyme.

Figure 11:
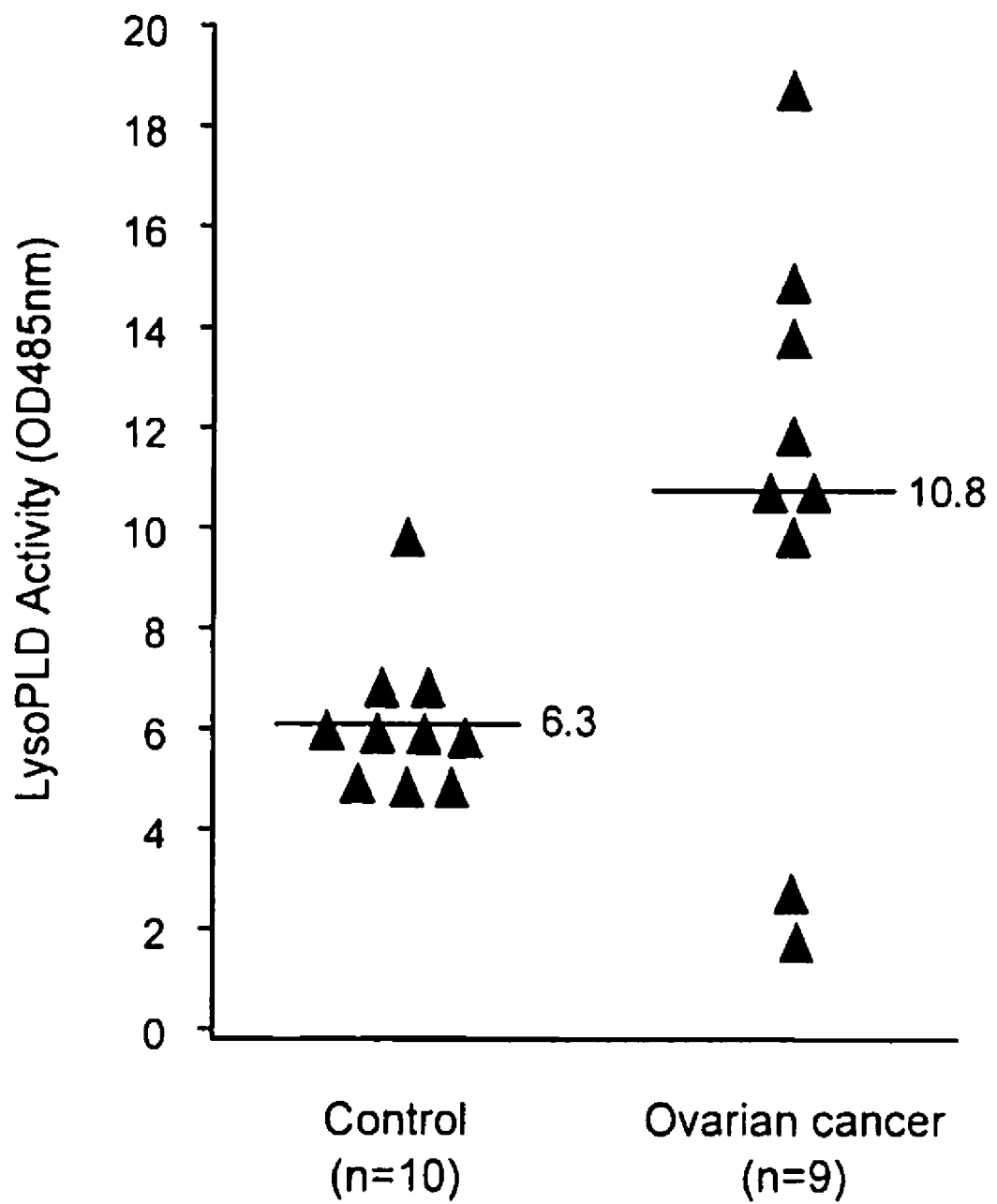
FIG. 11 demonstrates the turnover of FS-3 by ascites fluid of normal and ovarian cancer patients.

The substrates are also applicable to measuring the amount of ATX/LysoPLD activity in biological samples such as plasma, ascites fluid and serum. In particular, the assay could be used for diagnostic purposes by measuring enzyme levels in patient samples. This is demonstrated in FIG. 11. Ascites from patients with ovarian cancer and those without were tested. The samples were diluted to 10% (v/v) into PBS and added to the wells of a microtiter plate. A stock solution of FS-3 in PBS was added to each well so that the final concentration was 10 µM. Fluorescence was read at 523 nm after 6 hours. As shown in FIG. 11, there is a small but significant increase in activity measured in the ovarian cancer samples compared with the normals.

The following describes the synthetic steps and characterization of the intermediates for preparing the compounds FS-1, FS-2, ES-3, and FS-7 detailed in the present invention.

1-N-butoxycarbonyl-aminocaproyl-3-p-methoxybenzyl-glycerol (2). DCC (2.88 g, 14.0 mmol) and DMAP (0.76 g, 6.2 mmol) were added to a cooled (0° C.) solution of 1 (2.99, 14.0 mmol) and N-Boc-caproic acid (2.92 (12.2 mmol) in dry $CH_2Cl_2$ (50 mL) and the reaction mixture was stirred overnight at 4° C. The resulting white precipitate was filtered off and the filtrate was evaporated until dry. The residue was purified by flash column chromatography (FCC) (9:11 hexanes (Hex): ethyl acetate (EtOAc)). Yield: 2.79 g (49%). $R_F$=0.17 (1:1 Hex:EtOAc); $\delta_H$(CDCl$_3$): 7.25 (d, J=7.5 Hz, 2H), 6.88 (d, J=7.5 Hz, 2H), 4.55 (bs, 1H), 4.42 (s, 2H), 4.12-4.16 (m, 2H), 4.01 (quin, J=4.4 Hz, 1H), 3.80 (s, 3H), 3.48 (dd, J=15.6, 4.4, 1H), 3.45 (dd, J=9.6 Hz, 6.0 Hz, 1H), 3.09 (quart, J=7.1 Hz, 2H), 2.32 (t, J=7.2 Hz, 2H), 1.63 (quin, J=8.0 Hz, 2H), 1.46 (quin, J=8.0 Hz, 2H), 1.43 (s, 9H), 1.33 (quin, J=7.6 Hz, 2H).

1-N-butoxycarbonyl-aminocaproyl-2-tert-butyl-3-p-methoxybenzyl-glycerol (3). To a solution of 2 (510.1 mg, 1.19 mmol) and tert-butoxytrichloroacetamide (430 µL, 2.38 mmol) in cyclohexane (2 mL) and $CH_2Cl_2$ (1 mL) was added $BF_3$-$Et_2O$ (20 µL). The reaction was stirred under Ar for 16 hours. Solid $NaHCO_3$ was then added and the mixture was passed through a plug of silica. The crude product was purified by FCC (3:1 Hex:EtOAc). Yield: 508.5 mg (89%). $R_F$=0.30 (7:3 Hex:EtOAc); $\delta_H$(CDCl$_3$): 7.23 (d, J=7.5 Hz, 2H), 6.85 (d, J=7.5 Hz, 2H), 4.52 (bs, 1H), 4.45 (s, 2H), 4.17 (dd, J=10.8, 4.8 Hz, 1H), 4.05 (dd, J=11.6, 10.8), 3.82 (quin, J=5.2 Hz, 1H), 3.80 (s, 3H), 3.37-3.45 (m, 2H), 3.09 (m, 2H), 2.29 (t, J=7.1 Hz, 2H), 1.62 (m, 2H), 1.46 (quin, J=8.0 Hz, 2H), 1.42 (s, 9H), 1.33 (quin, J=7.6 Hz, 2H), 1.17 (s, 9H).

1-N-butoxycarbonyl-aminocaproyl-2-tert-butylglycerol (4). DDQ (281.2 mg, 1.23 mmol) was added to a solution of 3 (496.6 mg, 1.01 mmol) in 100:1 $CH_2Cl_2$:$H_2O$. The reaction mixture was stirred overnight and was then diluted with $CH_2Cl_2$, washed with saturated $NaHCO_3$, water and then brine, dried (MgSO$_4$), and evaporated. The product was purified by FCC (1:1 Hex:EtOAc). Yield: 82.7 mg (22%). $R_F$=0.24 (1:1 Hex:EtOAc); $\delta_H$(CDCl$_3$): 4.59 (bs, 1H), 4.15 (dd, J=11.4, 7.2 Hz, 1H), 4.05 (dd, J=11.4, 9.0 Hz, 1H), 3.77 (quin, J=5.8 Hz, 1H), 3.43-3.61 (m, 2H), 3.12 (t, J=8.5 Hz, 2H), 2.32 (t, J=9.1 Hz, 2H), 2.20 (bs, 1H), 1.63 (quin, J=10.3 Hz, 2H), 1.17-1.55 (m, 22H).

6-tert-Butoxycarbonylamino-hexanoic acid 3-[benzyloxy-(2-benzyloxycarbonylamino-ethoxy)-phosphoryloxy]-2-tert-butoxy-propyl ester(6). A solution of 5 (109.8 mg, 0.25 mmol) in $CH_2Cl_2$ (2 mL) was added to a solution of 4 (87.3 mg, 0.24 mmol) and 1H-tetrazole (84.0 mg, 1.2 mmol) in $CH_2Cl_2$ (1 mL) and then stirred for 1.5 hours at room temp. The solution was cooled to −40° C. and MCPBA (331.2 mg, 1.92 mmol) was added. The mixture was stirred for 5 min. The solution was allowed to warm to room temp. over 30 min. The reaction mixture was diluted with $CH_2Cl_2$, washed with sat'd $NaHCO_3$, dried (MgSO$_4$), and evaporated. The residue was purified by FCC (1:4 Hex EtOAc). $R_F$=0.33 (1:4 Hex:EtOAc); $\delta_P$(CDCl$_3$): 0.18.

6-tert-Butoxycarbonylamino-hexanoic acid 2-tert-butoxy-3-[(2-{1-[4-(4-dimethylamino-phenylazo)-phenyl]-vinylamino}-ethoxy)-hydroxy-phosphoryloxy]-propyl ester DABCYL-aminoethyl (N-Boc-aminocaproyl)-2-tert-butylglycerylphosphate (7). A suspension of 6 (31.2 mg, 0.044 mmol) and 10% Pd/C (104.0 mg) in 6:1 t-BuOH:$H_2O$ (20 mL) was shaken under an atmosphere of $H_2$ (50 psi) for 16 hrs. The mixture was filtered through a pad of Celite 545, the pad was washed with acetone:EtOAc, and the filtrate was evaporated until dry. Yield: 20.3 mg (95%). The crude amine (15.3 mg, 3.1 μmol) was dissolved in DMF (1 mL) and to it was added a solution of DABCYL-SE (13.5 mg, 3.7 μmol) in DMF (1 mL) followed by NEt$_3$ (13 μL). The reaction was stirred at room temperature overnight, then evaporated until dry and purified by FCC (7:3 CHCl$_3$:MeOH, 1% AcOH). ESI-MS: 734.1 ((M−H)$^-$, 100.0).

DABCYL-aminoethyl (N-BODIPY-FL®-aminocaproyl)-2-tert-buiylglycerylphosphate (FS-1). TFA (2 mL) was added to a solution of 7 in CH$_2$Cl$_2$ (5 mL) and stirred for 1 hour. The reaction was evaporated until dry [ESI-MS: 578.0 ((M−H), 100.0)]. The crude amine (6 mg) was dissolved in 0.5M TEAB (2 mL, pH 7.6). To it was added a solution of BODIPY-FL®-SE (5.2 mg, 12.4 mmol) in DMF (1 mL) and the reaction was stirred overnight at room temp. The solvents were evaporated and the product was purified by FCC (7:3 CHCl$_3$:MeOH). Yield: 7.5 mg (83%). R$_f$=0.15 (7:3 CHCl3:MeOH); FAB-MS: 880.4 ((M−H), 100.0).

{2-[2-(2-{2-[2-(2-Hydroxy-ethylcarbamoyl)-ethoxy]-ethoxy}-ethoxy)-ethoxy]-ethyl}-carbamic acid benzyl ester (8) Benzyl chloroformate (64 μL, 0.45 mmol) was added to a solution of PEG$_4$ amino acid in tetrahydrofuran (THF, 1 mL) and 1M NaOH (1 mL) and stirred for 3 hours. The reaction mixture was diluted with water, washed with ether, and then acidified to a pH of 2 with 2M HCl. The aqueous phase was extracted 3 times with EtOAc and the combined organic phases were washed with saturated aq. NaHCO$_3$, water and then brine, dried with MgSO$_4$, and then evaporated. Yield 125.8 mg (85%). DIC (22 μL, 0.14 mmol) was added to a solution of the crude product (57.1 mg, 0.14 mmol) and HOBt (19.9 mg, 0.15 mmol) in 9:1 CH$_2$Cl$_2$ (1 mL) and stirred for 15 minutes. Ethanolamine (17.1 mg, 0.28 mmol) was added and the reaction stirred at room temp for 4 hours. The reaction product was diluted with CH$_2$Cl$_2$, washed first with water and then brine, dried with MgSO$_4$, and evaporated. The residue was purified by FCC (9:1 CHCl$_3$:MeOH) to give 8. Yield 47.1 mg (76%). R$_F$=0.36 (9:1 CHCl$_3$:MeOH); δ$_H$(CDCl$_3$): 7.21-7.39 (m, 5H), 5.08 (s, 2H), 3.52-3.78 (m, 18H), 3.33-3.99 (m, 4H), 2.45 (m, 2H), 1.23 (d, 1H).

6-tert-Butoxycarbonylamino-hexanoic acid 3-(benzyloxy-{2-[3-(2-{2-[2-(2-benzyloxycarbonylamino-ethoxy)-ethoxy]-ethoxy}-ethoxy)-propionylamino]-ethoxy}-phosphoryloxy)-2-tert-butoxy-propyl ester (9). A solution of 4 (82.7 mg, 0.23 mmol) in CH$_2$Cl$_2$ was added to a solution of benzyl bisdiisopropylphosphoramidite (144.4 mg, 0.42 mmol) and tetrazole (7.5 mg, 0.11 mmol) in CH$_2$Cl$_2$ and stirred, for 1 hour. The solvent was evaporated and the residue was purified by FCC (4:1 H:EA, 5% TEA) to give the phosphoramidite. The phosphoramidite in CH$_2$Cl$_2$ (1 mL) was added to a solution of 8 (47.1 mg, 0.106 mmol) and tetrazole (34.9 mg, 0.5 mmol) in CH$_2$Cl$_2$ (1 mL) and stirred until the starting material had been consumed according to evaluation by TLC. The reaction was cooled to −40° C. and a solution of MCPBA (96.8 mg, 0.360 mmol) in CH$_2$Cl$_2$ was added dropwise. The reaction was stirred for 10 minutes and then allowed to warm to room temperature. It was diluted with CH$_2$Cl$_2$, washed with saturated aq. NaHCO$_3$, dried with MgSO$_4$, and evaporated. The residue was purified by FCC (19:1 CHCl$_3$:MeOH, 1% TEA) to give 10. (Yield 77.5 mg, 76%). δ$_H$(CDCl$_3$): 7.27-7.42 (m, 10H), 5.06-5.16 (m, 4H), 3.91-4.12 (m, 6H), 3.80-3.89 (m, 1H), 3.7 (t, 2H), 3.44-3.64 (m, 21H), 3.38 (t, 2H), 3.10 (t, 2H), 2.47 (t, 2H), 2.37 (td, 2H), 1.62 (m, 2H), 1.44 (M, 11H), 1.35 (m, 2H), 1.18 (s, 9H); δ$_C$(CDCl$_3$): 173.5, 171.9, 156.7, 136.8, 128.9, 128.8, 128.7, 128.3, 128.2, 128.2, 75.1, 70.7, 70.6, 70.5, 70.4, 70.2, 69.7, 67.9, 67.8, 67.2, 66.8, 64.2, 39.8, 39.7, 37.0, 34.2, 29.9, 28.6, 28.3, 28.2, 26.5, 24.7; δ$_P$(CDCl$_3$): 0.34, 0.31 (1:1).

6-tert-Butoxycarbonylamino-hexanoic acid 3-({2-[3-(2-{2-[2-(2-amino-ethoxy)-ethoxy]-ethoxy}-ethoxy)-propionylamino]-ethoxy}-hydroxy-phosphoryloxy)-2-tert-butoxypropyl ester (10). A suspension of 9 (30.2 mg, 0.0313 mmol) and 10% Pd/C (11.3 mg) in 6:1 t-BuOH:H$_2$O was shaken under an atmosphere of H$_2$ (50 psi) for 5.5 hours. The reaction was filtered through a pad of Celite 545 and the pad was washed with 6:1 t-BuOH:H$_2$O (10 mL) and EtOH (2×10 mL). The solvents were evaporated and the product was used in subsequent steps without further purification. R$_F$=0.59 (10:5:1 CHCl$_3$:MeOH:H$_2$O); δ$_H$(CD$_3$OD): 4.16 (dt, 1H), 4.05 (dd, 1H), 3.80-4.02 (m, 5H), 3.71-3.79 (m, 4H), 3.59-3.71 (m, 13H), 3.45 (m, 2H), 3.14 (t, 2H), 3.02 (t, 2H), 2.50 (t, 2H), 2.30-2.39 (m, 2H), 1.63 (quin, 2H), 1.47 (quin, 2H), 1.43 (s, 9H), 1.28-1.28 (m, 2H), 1.22 (s, 9H); δ$_P$(CD$_3$OD): 0.28; MALDI-MS: 732.4 ((M+H)$^+$, 100.0).

6-tert-Butoxycarbonylamino-hexanoic acid 2-tert-butoxy-3-{[2-(3-{2-[2-(2-{2-[4-(4-dimethylamino-phenylazo)-benzoylamino]-ethoxy}-ethoxy)-ethoxy]-ethoxy}-propionylamino) -ethoxy]-hydroxy-phosphoryloxy}-propyl ester (11). NEt$_3$ (0.1 mL) was added to a solution of 10 (11.2 mg, 15.3 μmol) and DABCYL-NHS (8.5 mg, 23.2 μmol) in DMF (2 mL). The reaction was stirred overnight, evaporated until dry and purified by FCC (40:10:1-10:5:1 CHCl$_3$:MeOH: H$_2$O). 11 was obtained as an orange solid (yield: 9.0 mg, 60%). R$_F$=0.21 (40:10:1 CHCl$_3$:MeOH:H$_2$O); δ$_H$(CD$_3$OD): 7.96 (d, 2H), 7.85 (d, 2H), 7.84 (d, 2H), 6.84 (d, 2H), 4.20 (dd, 1H), 4.03 (dd, 1H), 3.81-3.95 (m, 5H), 3.56-3.79 (m, 15H), 3.40 (m, 2H), 3.10 (s, 6H), 3.00 (t, 2H), 2.45 (t, 2H), 2.14 (t, 2H), 1.60 (quin, 2H, 1.45 (quin, 2H), 1.42 (s, 9H), 1.27-1.35 (m, 2H), 1.20 (s, 9H); δ$_P$(CD$_3$OD): 1.01; MALDI-MS: 1005.6 (M+Na)$^+$.

FS-2. TFA (0.5mL) was added to a solution of 11 (9.0 mg, 9.2 μmol) in CH$_2$Cl$_2$ (2 mL) and the reaction was stirred for 1 hour in the dark. The solvents were evaporated and the crude amine product was dissolved in 0.5M TEAB (1 mL) and DMF (1 mL). A solution of BODIPY-FL®-NHS (4.5 mg, 10.8 μmol) in DMF (1 mL) was add and the reaction was stirred for 4 hours at room temperature in the dark. The solvents were evaporated and the residue was purified by FCC (40:10:1-10:5:1 CHCl$_3$:MeOH:H$_2$O). 12 was obtained as a orange solid (yield: 10.3 mg, 91%). R$_F$ = 0.21 (10:5:1 CHCl$_3$:MeOH: H$_2$O); δ$_H$(CD$_3$OD): 7.95 (d, 2H), 7.84 (d, 2H), 7.82 (d, 2H), 7.37 (s, 1H), 7.05 (d, 1H), 6.82 (d, 2H), 6.31 (d, 1H), 3.16 (s, 1H), 4.11 (dd, 2H), 3.81-4.00 (m, 5H), 3.53-3.72 (m, 15H), 3.40 (t, 2H), 3.10 (s, 6H), 2.48 (s, 3H), 2.45 (t, 2H), 2.32 (t, 2H), 2.25 (s, 3H), 2.20 (s, 3H), 1.67-1.79 (m, 4H), 1.60 (quin, 2H), 1.48 (quin, 2H), 1.34 (m, 2H);δ$_P$(CD$_3$OD): 1.62; MALDI-MS:1173.8 (M−H+2Na)$^+$.

N-{2-[2-(2-{2-[2-(2-{[2-tert-Butoxy-3-(6-tert-butoxycarbonylamino -hexanoyloxy)-propoxy]-hydroxy-phosphoryloxy}-ethylcarbamoyl)-ethoxy]-ethoxy}-ethoxy)-ethoxy]-ethyl}-6-(6-hydroxy-3-oxo-3H-xanthen-9-yl)-isophthalamic acid (12). NEt$_3$ (0.1 mL) was added to a solution of 10 (11.2 mg, 15.3 μmol) and fluorescein-NHS (11.6 mg, 24.5 μmol) in DMF (2 mL). The product was purified by FCC (65:25:4 CHCl$_3$:MeOH:H$_2$O). Yield: 11.3 mg (68%). R$_F$=0.21 (65:25:4 CHCl$_3$:MeOH:H$_2$O); δ$_H$(CD$_3$OD): 4.19 (d, 2H), 4.03 (d, 2H), 3.78-3.96 (m, 5H) 3.34-3.77 (m, 17H), 3.01 (t, 2H), 2.42 (dt, 2H), 2.32 (t, 2H), 1.60 (quin, 2H), 1.45 (quin, 2H), 1.41 (s, 9H), 1.27-1.25 (m, 2H), 1.19 (s, 9H); δ$_P$(CD$_3$OD): 1.27; MALDI-MS: 1113.6 (M+Na)$^+$.

FS-3. TFA (0.5 mL) was added to a solution of 11 (9.0 mg, 9.2 μmol) in $CH_2Cl_2$ (2 mL) and the reaction was stirred for 1 hour in the dark. The solvents were evaporated and the crude amine product was dissolved in 0.5M TEAB (1 mL) and DMF (1 mL). A solution of DABCYL-NHS (4.9 mg, 13.3 μmol) in DMF (1 mL) was added and the reaction was stirred for 4 hours at room temperature in the dark. The solvents were evaporated and the residue was purified by FCC (40:10:1-10:5:1 $CHCl_3$:MeOH:$H^2O$). Yield: 6.4 mg (52%). $R_F$=0.31 (10:5:1 $CHCl_3$:MeOH:$H_2O$); $\delta_H$($CD_3OD$): 7.92 (d, 2H), 7.80-7.85 (m, 4H), 6.82 (d, 2H), 6.52-6.71 (m, 5H), 4.12 (dd, 2H), 3.81-3.99 (m, 5H), 3.43-3.72 (m, 20H), 3.39 (t, 2H), 3.09 (s, 6H), 2.43 (m, 2H), 2.37 (t, 2H), 1.61-1.70 (m, 4H), 1.42 (quin, 2H); $\delta_P$($CD_3OD$): 1.76; MALDI-MS: 1230.7 (M−H+2Na)$^+$.

3-N-Boc-aminohexyl-2-tert-butyldimethylsilyl-1-toluensulfonyl-sn-glycerol (13). $BF_3$-$Et_2O$ (17.4 μL.) was added to a solution of (S)-toluenesulfonyl-glycidol (239.4 mg, 1.05 mmol) and 6-N-Boc-aminohexanol (346.0 mg, 1.59 mmol) in $CH_2Cl_2$ (5 mL), the solution was stirred at room temperature for 14 hours and then refluxed for 6 hours. The solvent was evaporated and passed through a plug of silica gel and eluted with 19:1 $CH_2Cl_2$:MeOH. The product (226 mg, ~0.598 mmol) was dissolved in DMF (2 mL) with $NEt_3$ (120 mg, 1.19 mmol), and DMAP (134 mg, 1.19 mmol). TBDMSCl (135 mg, 0.897 mmol) was added and the reaction was stirred overnight at room temperature. The reaction mixture was diluted with EtOAc, washed first with water and then brine, dried with $MgSO_4$, and evaporated. The residue was purified by FCC (17:3 Hex:EtOAc). Yield: 100 mg. $\delta_H$($CDCl_3$): 7.76 (d, 2H), 7.31 (d, 2H), 4.54 (bs, 1H), 4.03 (d, 1H), 3.85-3.97 (m, 2H), 3.27-3.35 (m, 4H), 3.07 (t, 2H), 2.41 (s, 3H), 1.33-1.52 (m, 11H), 1.27 (m, 2H), 0.80 (s, 9H), 0.01 (s, 6H).

The substrates disclosed in the present invention are preferably specific for LysoPLD. However, some of the substrates included in this invention may be metabolized by other enzymes with phospholipase activity. For instance, enzymes with lysophospholipase $A_1$ activity, which cleaves the sn-1 acyl chain from phospholipids, could react with certain substrates such as FS-1, FS-2, FS-3 or any substrate described in FIG. 3 in which Y=O and X=C(O). Other substrates in which the acyl ester is replaced by a more robust linkage such as an ether, amide, or methylene would be resistant to such enzymes.

One embodiment of the present invention is an in vitro assay for measuring LysoPLD activity. As an example, a black 96-well plate is used although the invention is clearly adaptable to a variety of assay plate sizes and formats. Initially a standard curve is determined to establish a range of measurable enzyme concentrations. Enzymes can be obtained by purification from plasma, media from cells overexpressing LysoPLD, or a recombinant tagged construct. For example, 10 μL of a 50 μM stock solution of the substrate is added to the wells of a black 96-well plate containing 39 μL buffer so the final concentration of the substrate is 10 μM. Initial fluorescent readings without enzyme using an excitation of 485 nm and emission of 523 nm (for green fluorophores such as fluorescein for instance) are taken to establish the background level. Aliquots (1 μL) of stock solutions of serially diluted LysoPLD are added to the wells and the reaction is allowed to proceed for a set amount of time (e.g. 4 hours) and a final measurement is taken. Plotting fluorescence vs. enzyme concentration will give a standard curve. The standard curve can be used to determine enzyme levels in unknown solutions. An aliquot of the unknown enzyme solution is added to a well containing a buffer and substrate. After 4 hours, the fluorescence is measured and plotting against the standard curve will yield the concentration of the unknown enzyme solution. The assay described above implies the substrate has a green fluorophore, however a substrate with any fluorophore is implied in addition to the optimal excitation and emission wavelengths being used in the assay.

The assays of present invention can be used for determining LysoPLD levels in biological fluids as a diagnostic means for detecting certain types of cancer. RNA levels of LysoPLD/ATX are known to be increased in certain types of cancer suggesting that measuring enzyme levels could be a prognostic indicator for that cancer. In the present invention, the substrates described are proposed to be used for determining the level of LysoPLD activity in biological solutions. Biological solutions can include but are not limited to plasma, serum, and ascities. As an example, a black 96-well plate is used although the invention is clearly adaptable to a variety of assay plate sizes and formats. A standard curve is established as described previously for the in vitro assay. An aliquot of the biological sample is diluted into a well containing reaction buffer and the substrate to a final concentration between 1-50%. After incubation at 37° C. for four hours, the fluorescence is measured (excitation 485 nm, emission 523 nm) and plotted on the standard curve to determine the amount of enzyme activity in the biological samples. All measurements are taken in triplicate. Comparison of levels between diseased and normal patient samples could give an indication whether increased enzyme activity correlates with the disease state.

The LysoPLD activity of ATX is increased in numerous types of cancer such as ovarian, prostate, breast, lung, colon, Hodgkin's lymphoma, and renal cell carcinoma. The assay described could be used for disease diagnosis and monitoring levels during treatment could be an indicator of the patient's progress. In addition, the present invention can be used to monitor the status of a patient receiving a medication designed to alter the activity of LysoPLD in a pharmaceutical context. Since LysoPLD activity is also a part of normal physiology, the described assay could be used for monitoring normal levels. For example, LysoPLD activity increases during the third trimester of pregnancy (Tokumura et al. Biology of Reproduction, 67:1386-1392, (2002)) and this described invention could be used for monitoring LysoPLD levels and thus pregnancy status.

Since the action of ATX/lysoPLD is recognized as an important factor in ovarian and other types of cancer, it becomes an attractive target for drug discovery efforts. Attenuating the activity of the enzyme offers another route to treating the disease. Using the fluorescent LysoPLD substrates and in vitro assay of the present invention, libraries of small molecules can be screened to find inhibitors of the enzyme. The assay method of the present invention can be adapted to high throughput screening. Automation of the assay can be performed using an automated liquid handling system interfaced to a fluorescence plate reader. The system would require a multichannel-pipettor for highly accurate and simultaneous dispensing of microvolumes of reagents in a large number of plates, such as 96-, 384- and 1536-well formats. Transfer to the analyzer, sample analysis, and data collection would be automated and computer controlled. The following describes a method for discovery of small molecule inhibitors. An aliquot (1 μL) of a solution, of the potential inhibitors in DMSO is added to 24 μL of a solution of buffer and substrate (10 mM final concentration) in the wells of a 384-well plate. An aliquot (1 μL) of LysoPLD stock solution of a desired concentration is added and the reaction is allowed to proceed for four hours at 25° C. Fluorescence is read (excitation 485 nm, emission 523 nm) and compared to a control well where only DMSO was added. Lower levels of fluorescence compared with the control indicate that the enzyme is being inhibited and a "hit" had been discovered. All measurements are taken in triplicate. The preceding description has been presented only to illustrate and describe the invention. The preferred embodiment was chosen and described in order to best explain the principles of the invention and its practical applications. The preceding description is intended to enable others skilled in the art to best utilize the invention in various embodiments and with various modifications as suited to the particular use contemplated. It will be apparent to those of ordinary skill in the art that numerous modifications can be made without departing from the principles and concepts of the invention as set forth in the claims.

What is claimed is:

1. A method for assaying the lysophospholipase D (LysoPLD) activity of autotoxin (ATX) comprising the steps of:
   a) obtaining a solution having ATX present;
   b) adding a LysoPLD substrate comprising a lysophospholipid derivative labeled with a fluorescent group and a quencher group to said solution containing ATX; and
   c) determining if LysoPLD activity is present in said solution by measuring the change in the fluorescent signal in said solution that is generated by the cleavage of said lysophospholipid derivative represented by the formula:

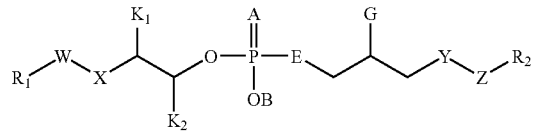

wherein A represents O or S; B represents H, Na$^+$, K$^+$, Li$^+$ or an alkyl group having 1-20 carbon atoms; E represents O, CH$_2$, CHF or CF$_2$; G represents H, OH, F, O-acyl or O-alkyl having 1-20 carbon atoms; K$_1$ and K$_2$ each represent H, F, alkyl having 1 to 20 carbon atoms, OH or CO$_2$H; W is C(O), NH(CH$_2$CH$_2$O)$_q$C(O) or (NHC(O)(CH$_2$)$_n$)$_p$C(O), wherein q is an integer from 1 to 33; n is an integer from 1 to 12; and p is an integer from 1 to 20; X represents NH; Y represents O, S or NH; Z is C(O)(CH$_2$)$_n$(C)NH, (CH$_2$CH$_2$O)$_q$C(O)NH or (CH$_2$)$_n$NH wherein n is an integer from 1 to 33; and R$_1$ and R$_2$ are a fluorescent group or a quencher, respectively.

2. The method according to claim 1, wherein said assay is a plate-based assay employing a multi-well microtiter plate.

3. The method according to claim 1, wherein the assay is a fluorescence resonance energy transfer(FRET) assay or time-resolved fluorescence resonance energy transfer(TR-FRET) assay.

4. The method according to claim 1, wherein said lysophospholipid derivative is a member selected from the group consisting of:

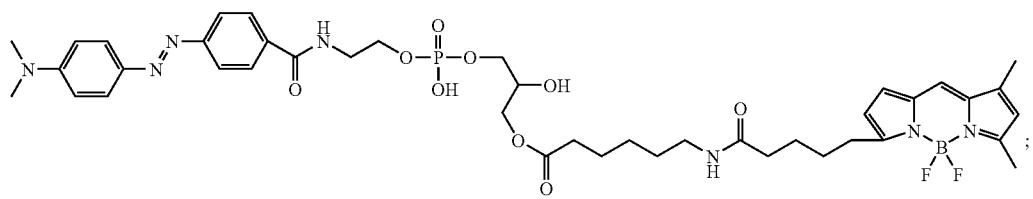

FS-1

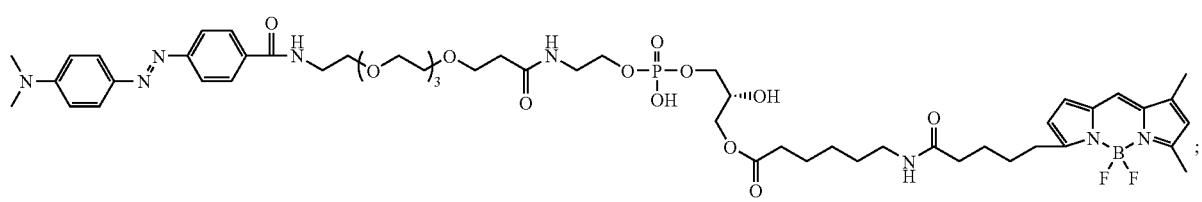

FS-2

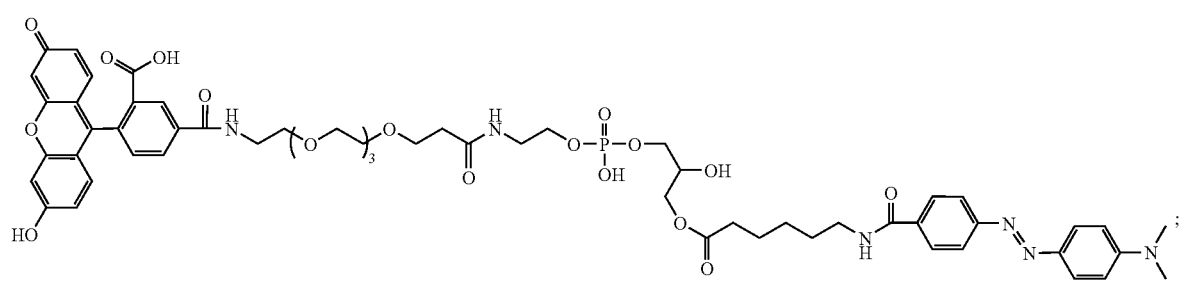

FS-3 and

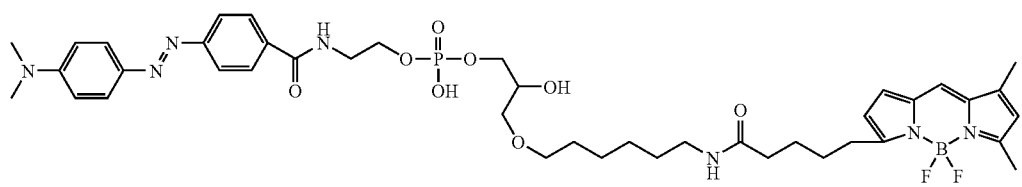

FS-7

5. A method of screening for breast cancer, lung cancer, ovarian cancer, prostate cancer, colon cancer, renal cell carcinomas, and Hodgkin's lymphoma comprising determining the level of LysoPLD activity of ATX in bodily tissue, blood, or serum samples using the method of claim 1.

6. A method for determining the status of breast cancer, lung cancer, ovarian cancer, prostate cancer, colon cancer, renal cell carcinomas, and Hodgkin's lymphoma comprising monitoring levels of Lyso PLD activity of ATX in bodily tissue, blood, or serum samples using the method of claim 1.

* * * * *